US007943320B2

(12) United States Patent
Cao

(10) Patent No.: US 7,943,320 B2
(45) Date of Patent: May 17, 2011

(54) UNSYMMETRICAL CYANINE DYES FOR HIGH RESOLUTION NUCLEIC ACID MELTING ANALYSIS

(75) Inventor: Weidong Cao, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 12/346,260

(22) Filed: Dec. 30, 2008

(65) Prior Publication Data

US 2010/0167279 A1    Jul. 1, 2010

(51) Int. Cl.
*C12Q 1/68*    (2006.01)
*C12P 19/34*    (2006.01)
*C07H 21/00*    (2006.01)
*C07D 279/00*    (2006.01)
*G03G 13/00*    (2006.01)
*G03G 15/08*    (2006.01)

(52) U.S. Cl. ......... 435/6; 435/91.1; 435/91.2; 536/23.1; 536/24.3; 536/24.33; 536/26.6; 544/14; 430/31; 430/93

(58) Field of Classification Search ............. 435/6, 91.1, 435/91.2; 536/23.1, 24.3, 24.33, 26.6; 544/14; 430/31, 93
See application file for complete search history.

(56) References Cited

U.S. PATENT DOCUMENTS

| 4,883,867 | A | 11/1989 | Lee et al. |
| 4,937,198 | A | 6/1990 | Lee et al. |
| 5,321,130 | A | 6/1994 | Yue et al. |
| 5,436,134 | A | 7/1995 | Haugland et al. |
| 5,563,070 | A | 10/1996 | Yamamoto et al. |
| 5,658,751 | A | 8/1997 | Yue et al. |
| 5,863,753 | A | 1/1999 | Haugland et al. |
| 6,004,816 | A | 12/1999 | Mizukami et al. |
| 6,015,902 | A | 1/2000 | Bieniarz et al. |
| 6,054,272 | A | 4/2000 | Glazer et al. |
| 6,080,868 | A | 6/2000 | Lee et al. |
| 6,329,144 | B1 | 12/2001 | Kubista et al. |
| 6,368,864 | B1 | 4/2002 | Deka et al. |
| 6,664,047 | B1 | 12/2003 | Haugland et al. |
| 2002/0197630 | A1 | 12/2002 | Knapp et al. |
| 2005/0233335 | A1 | 10/2005 | Wittwer et al. |
| 2006/0019253 | A1 | 1/2006 | Wittwer et al. |
| 2007/0020672 | A1 | 1/2007 | Wittwer et al. |
| 2007/0026421 | A1 | 2/2007 | Sundberg et al. |
| 2007/0231799 | A1 | 10/2007 | Knight et al. |
| 2008/0003588 | A1 | 1/2008 | Hasson et al. |
| 2008/0130971 | A1 | 6/2008 | Hasson et al. |
| 2008/0176230 | A1 | 7/2008 | Owen et al. |

FOREIGN PATENT DOCUMENTS

WO    2008/052742 A1    5/2008

*Primary Examiner* — Jezia Riley
(74) *Attorney, Agent, or Firm* — Rothwell, Figg, Ernst & Manbeck, PC

(57) ABSTRACT

The present invention relates to novel unsymmetrical cyanine dyes and to methods of performing nucleic acid analysis in the presence of such dyes. More specifically, the present invention relates to novel unsymmetrical cyanine dyes that have high affinity to double-stranded nucleic acids and that do not inhibit amplification reactions, particularly the polymerase chain reaction (PCR).

19 Claims, No Drawings

UNSYMMETRICAL CYANINE DYES FOR HIGH RESOLUTION NUCLEIC ACID MELTING ANALYSIS

BACKGROUND

1. Field of the Invention

The present invention relates to novel unsymmetrical cyanine dyes and to methods of performing nucleic acid analysis in the presence of such dyes. More specifically, the present invention relates to novel unsymmetrical cyanine dyes that have high affinity to double-stranded nucleic acids acid that do not inhibit amplification reactions, particularly the polymerase chain reaction (PCR).

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three-phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR, see *Real-Time PCR: An Essential Guide*, K. Edwards et al., eds., Horizon Bioscience, Norwich, U.K. (2004).

Melt curve analysis is an important technique for analyzing nucleic acids. In this method, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, for example, Ririe et al. (*Anal Biochem* 245:154-160, 1997), Wittwer et al. (*Clin Chem* 49:853-860, 2003), Liew et al. (*Clin Chem* 50:1156-1164 (2004), Herrmann et al. (*Clin Chem* 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Wittwer et al. (U.S. Patent Application Publication No. 2007/0020672) and Sundberg et al. (U.S. Patent Application Publication No. 2007/0026421).

Unsymmetrical cyanine dyes are a group of dyes which have been used in nucleic acid and protein staining. Additional unsymmetrical cyanine dyes have been developed which have been used for binding to RNA and/or DNA. See, for example, Lee et al. (U.S. Pat. No. 4,883,867), Lee et al. (U.S. Pat. No. 4,937,198), Yue et al. (U.S. Pat. No. 5,321,130), Wittwer et al. (U.S. Patent Application Publication No. 2006/0019253), Wittwer et al. (U.S. Patent Application Publication No. 2007/0020672), Haugland et al. (U.S. Pat. No. 5,436,134), Yamamoto et al. (U.S. Pat. No. 5,563,070), Yue et al. (U.S. Pat. No. 5,658,751), Mizukami et al. (U.S. Pat. No. 6,004,816), Bieniarz et al. (U.S. Pat. No. 6,015,902), Glazer et al. (U.S. Pat. No. 6,054,272), Lee et al. (U.S. Pat. No. 6,080,868), Kubista et al. (U.S. Pat. No. 6,329,144), Deka et al. (U.S. Pat. No. 6,368,864) and Haugland et al. (U.S. Pat. No. 6,664,047).

Several problems exist with known unsymmetrical cyanine dyes. For example, certain unsymmetrical cyanine dyes can poison the PCR reaction. Other unsymmetrical cyanine dyes suffer from weak binding to nucleic acids. Still other unsymmetrical cyanine dyes both poison the PCR reaction and weakly bind to nucleic acids. These and other drawbacks of unsymmetrical cyanine dyes currently exit.

SUMMARY OF THE INVENTION

The present invention relates to novel unsymmetrical cyanine dyes and to methods of performing nucleic acid analysis in the presence of such dyes. More specifically, the present invention relates to novel unsymmetrical cyanine dyes that have high affinity to double-stranded nucleic acids and that do not inhibit amplification reactions, particularly the polymerase chain reaction (PCR).

Thus, in a first aspect, the present invention provides novel unsymmetrical cyanine dyes. In one embodiment, the unsymmetrical cyanine dyes are the compounds of Formula I:

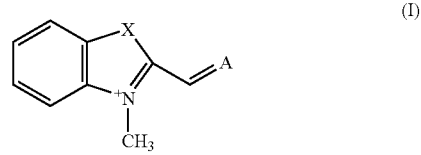

wherein A is

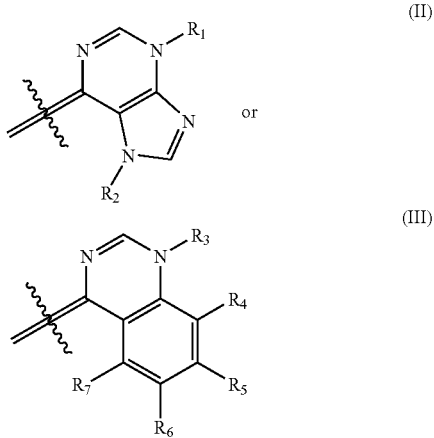

wherein X is O or S, $R_1$, $R_2$, $R_3$, $R_4$, $R_5$, $R_6$ and $R_7$ are independently hydrogen, halogen, thiol, optionally substituted alkyl, optionally substituted alkoxy, optionally substituted alkenyl, optionally substituted polyalkenyl, optionally substituted alkynyl, optionally substituted polyalkynyl, optionally substituted thioalkyl, optionally substituted aminoalkyl, optionally substituted aryl, optionally substituted heteroaryl and optionally substituted arylalkyl, $R_1$ and/or $R_2$ carry one or more positive charges such that the sum of the positive charge(s) on $R_1$ and $R_2$ is 1, 2 or 3, and $R_3$, and/or $R_4$, and/or $R_5$, and/or $R_6$ and/or $R_7$ carry one or more positive charges such that the sum of the positive charge(s) on $R_3$, $R_4$, $R_5$, $R_6$ and $R_7$ is 1, 2 or 3.

The alkyl may be a straight or branched chain and may contain 1-12 carbons. The alkoxy may be a straight or branched chain and may contain 1-12 carbons. The alkenyl may be a straight or branched chain and may contain 2-12 carbons. The alkynyl may be a straight or branched chain and may contain 2-12 carbons. The polyalkenyl may be a straight or branched chain and may contain 4-12 carbons. The polyalkynyl may be a straight or branched chain and may contain 4-12 carbons. The thioalkyl may be a straight or branched chain, may contain 1-12 carbons and is linked to the parent molecule through the alkyl group. The aminoalkyl may be a straight or branched chain, may contain 1-12 carbons and is linked to the parent molecule through the alkyl group. The aryl may be an aromatic monocyclic or multicyclic ring system comprising about 6 to about 14 carbon atoms. The heteroaryl may be an aromatic monocyclic or multicyclic ring system comprising about 5 to about 14 ring atoms in which one or more of the ring atoms is an element other than carbon, for example, nitrogen, oxygen or sulfur, alone or in combination. The alkyl in the arylalkyl may be straight or branched chain and may contain 1-12 carbons. The arylalkyl is linked to the parent molecule through the alkyl group.

The optional substituents may include one or more substituents which may independently be halo, hydroxyl, amino, thiol, alkyl, cycloalkyl, haloalkyl, halocycloalkyl, alkoxy, cycloalkoxy, haloalkoxy, alkylaminodialkyl, alkylaminotrialkyl, alkylthio, haloalkyl, cycloalkyl, arylcarbonyl, arylsulfonyl, optionally substituted heterocyclyl and carboxyl derivatives, such as carboxylic acids, esters, and amides, or other substituents described herein. The heterocyclyl may be a non-aromatic saturated monocyclic or multicyclic ring system comprising about 3 to about 10 ring atoms in which one or more of the atoms in the ring system is an element other than carbon, for example, nitrogen, oxygen or sulfur, alone or in combination.

In one embodiment, the positive charge(s) on $R_1$ and $R_2$, or on $R_3$, $R_4$, $R_5$, $R_6$ and $R_7$ arises from a substituent on the unsymmetrical cyanine dye that has a positive charge in the native configuration. In another embodiment, the positive charge(s) on $R_1$ and $R_2$, or on $R_3$, $R_4$, $R_5$, $R_6$ and $R_7$ arises from a substituent or substituents that have a positive charge at the pH for which an amplification reaction, such as a polymerase chain reaction, is conducted.

In one embodiment, A has the structure of Formula II. In some embodiments, $R_1$ is aryl, alkyl substituted with dialkylamino, alkyl substituted with trialkylamino, alkyl substituted with alkoxy, alkyl substituted with alkoxy that is substituted with dialkylamino, or alkyl substituted with an N-substituted heterocyclyl, and $R_2$ is hydrogen, alkyl, thiol, alkyl substituted with trialkylamino or alkyl substituted with alkoxy.

In another embodiment, A has the structure of Formula III. In some embodiments, $R_3$ is hydrogen, methyl, alkyl substituted with trialkylamino or alkyl substituted with an N-substituted heterocyclyl, $R_4$ is hydrogen, alkyl, aryl, thiol, alkyl substituted with dialkyamino, alkyl substituted with trialkylamino, alkyl substituted with alkoxy that is substituted with dialkylamino, or alkyl substituted with an N-substituted heterocyclyl, $R_5$ is hydrogen, halo, alkyl, aryl or alkyl substituted with alkoxy that is substituted with dialkylamino, $R_6$ is hydrogen, alkyl, alkyl substituted with trialkylamino or alkyl substituted with an N-substituted heterocyclyl and $R_7$ is hydrogen, alkyl or alkyl substituted with alkoxy.

In a second aspect, the present invention provides a method of performing nucleic acid analysis in the presence of the novel unsymmetrical cyanine dyes of the present invention. In one embodiment, the method comprises the steps of: mixing an unsymmetrical cyanine dye of the present invention with a sample comprising a target nucleic acid and one or more primers configured for amplifying the target nucleic acid, amplifying the target nucleic acid in the presence of the unsymmetrical cyanine dye, and monitoring fluorescence of the unsymmetrical cyanine dye. In another embodiment, the monitoring step comprises melting the amplified target nucleic acid to generate a melting curve. In a further embodiment, the target nucleic acid comprises a single nucleotide polymorphism. In an additional embodiment, the method further comprises identifying a genotype on the basis of the monitored fluorescence. In one embodiment, the genotype is identified on the basis of the melting curve. In another embodiment, the amplification and monitoring occur in a microfluidic channel. In one embodiment, the monitoring step occurs during the amplification step. In another embodiment, the monitoring step occurs subsequent to the amplification step. In a further embodiment, the monitoring occurs during the amplification step and subsequent to the amplification step. In one embodiment, the monitoring step subsequent to the amplification step comprises melting the amplified target nucleic acid to generate a melting curve.

DETAILED DESCRIPTION OF THE INVENTION

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

The present invention relates to novel unsymmetrical cyanine dyes and to methods of performing nucleic acid analysis in the presence of such dyes. More specifically, the present invention relates to novel unsymmetrical cyanine dyes that have high affinity to double-stranded nucleic acids and that do not inhibit amplification reactions, particularly the polymerase chain reaction (PCR).

Thus, in one aspect, the present invention provides novel unsymmetrical cyanine dyes. In one embodiment, the unsymmetrical cyanine dyes are the compounds of Formula I:

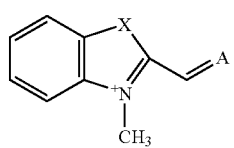

(I)

wherein A is

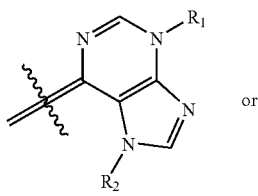

(II)

or

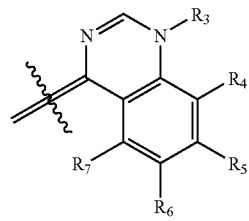

(III)

wherein X is O or S, $R_1$, $R_2$, $R_3$, $R_4$, $R_5$, $R_6$ and $R_7$ are independently hydrogen, halogen, thiol, optionally substituted alkoxy, optionally substituted thioalkyl, optionally substituted aminoalkyl, optionally substituted alkyl, optionally substituted alkenyl, optionally substituted polyalkenyl, optionally substituted alkynyl, optionally substituted polyalkynyl, optionally substituted aryl, optionally substituted heteroaryl, optionally substituted arylalkyl and optionally substituted heteroarylalkyl, $R_1$ and/or $R_2$ carry one or more positive charges such that the sum of the positive charge(s) on $R_1$ and $R_2$ is 1, 2 or 3, and $R_3$, and/or $R_4$, and/or $R_5$, and/or $R_6$ and/or $R_7$ carry one or more positive charges such that the sum of the positive charge(s) on $R_3$, $R_4$, $R_5$, $R_6$ and $R_7$ is 1, 2 or 3.

"Alkyl" means an aliphatic hydrocarbon group which may be straight or branched and comprises about 1 to about 12 carbon atoms in the chain, preferably about 1 to about 8 carbon atoms in the chain. Branched means that one or more lower alkyl groups such as methyl, ethyl or propyl, are attached to a linear alkyl chain. "Lower alkyl" means a group having about 1 to about 5 carbon atoms in the chain which may be straight or branched. "Alkyl" may be unsubstituted or optionally substituted by one or more substituents which may be the same or different, each substituent being independently selected from those described herein.

"Alkenyl" means an aliphatic hydrocarbon group containing at least one carbon-carbon double bond and which may be straight or branched and comprises about 2 to about 12 carbon atoms in the chain, preferably about 2 to about 8 carbon atoms in the chain. Branched means that one or more lower alkyl groups such as methyl, ethyl or propyl, are attached to a linear alkenyl chain. "Lower alkenyl" means about 2 to about 5 carbon atoms in the chain which may be straight or branched. "Alkenyl" may be unsubstituted or optionally substituted by one or more substituents which may be the same or different, each substituent being independently selected from those described herein.

"Alkynyl" means an aliphatic hydrocarbon group containing at least one carbon-carbon triple bond and which may be straight or branched and comprises about 2 to about 12 carbon atoms in the chain, preferably about 2 to about 8 carbon atoms in the chain. Branched means that one or more lower alkyl groups such as methyl, ethyl or propyl, are attached to a linear alkynyl chain. "Lower alkynyl" means about 2 to about 5 carbon atoms in the chain which may be straight or branched. "Alkynyl" may be unsubstituted or optionally substituted by one or more substituents which may be the same or different, each substituent being independently selected from those described herein.

"Aryl" means an aromatic monocyclic or multicyclic ring system comprising about 6 to about 14 carbon atoms, preferably about 6 to about 10 carbon atoms. The aryl group can be optionally substituted with one or more substituents which may be the same or different, each substituent being independently selected from those described herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. The "heteroaryl" can be optionally substituted by one or more substituents which may be the same or different, each substituent being independently selected from those described herein. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Arylalkyl" means an aryl-alkyl-group in which the aryl and alkyl are as previously described. The bond to the parent moiety is through the alkyl.

"Cycloalkyl" means a non-aromatic mono- or multicyclic ring system comprising about 3 to about 10 carbon atoms. The cycloalkyl can be optionally substituted with one or more substituents which may be the same or different, each substituent being independently selected from those described herein.

"Halogen" means fluorine, chlorine, bromine, or iodine.

"Heteroarylalkyl" means a heteroaryl-alkyl group in which the heteroaryl and alkyl are as previously described. The bond to the parent moiety is through the alkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. The heterocyclyl can be optionally substituted by one or more substituents which may be the same or different, each substituent being independently selected from those described herein. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system.

"Alkoxy" means an alkyl-O— group in which the alkyl group is as previously described. The alkoxy can be optionally substituted by one or more substituents which may be the same or different, each substituent being independently selected from those described herein. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. The bond to the parent moiety is through the ether oxygen.

"Arylalkoxy" means an arylalkyl-O— group in which the arylalkyl group is as previously described. The bond to the parent moiety is through the ether oxygen.

"Cycloalkyloxy" means a cycloalkyl-O— group in which the cycloalkyl group is as previously described. The bond to the parent moiety is through the ether oxygen.

"Heteroaryloxy" means a heteroaryl-O— group in which the heteroaryl group is as previously described. The bond to the parent moiety is through the ether oxygen.

"Heteroarylalkyloxy" means a heteroarylalkyl-O— group in which the heteroarylalkyl group is as previously described. The bond to the parent moiety is through the ether oxygen.

"Alkylthio" means an alkyl-S— group in which the alkyl group is as previously described. The alkylthio can be optionally substituted by one or more substituents which may be the same or different, each substituent being independently selected from those described herein. Non-limiting examples of suitable alkylthio groups include methylthio and ethylthio. The bond to the parent moiety is through the sulfur.

"Arylthio" means an aryl-S— group in which the aryl group is as previously described. The bond to the parent moiety is through the sulfur.

"Arylalkylthio" means an arylalkyl-S— group in which the arylalkyl group is as previously described. The bond to the parent moiety is through the sulfur.

"Cycloalkylthio" means a cycloalkyl-S— group in which the cycloalkyl group is as previously described. The bond to the parent moiety is through the sulfur.

"Heteroarylthio" means a heteroaryl-S— group in which the heteroaryl group is as previously described. The bond to the parent moiety is through the sulfur.

"Heteroarylalkylthio" means a heteroarylalkyl-S— group in which the heteroarylalkyl group is as previously described. The bond to the parent moiety is through the sulfur.

"Alkylcarbonyl" means an alkyl-C(O)— group in which the alkyl group is as previously described. The bond to the parent moiety is through the carbonyl.

"Arylcarbonyl" means an aryl-C(O)— group in which the aryl group is as previously described. The bond to the parent moiety is through the carbonyl.

"Arylalkylcarbonyl" means an arylalkyl-C(O)— group in which the arylalkyl group is as previously described. The bond to the parent moiety is through the carbonyl.

"Heteroarylcarbonyl" means a heteroaryl-C(O)— group in which the heteroaryl group is as previously described. The bond to the parent moiety is through the carbonyl.

"Heteroarylalkylcarbonyl" means a heteroarylalkyl-C(O)— group in which the heteroarylalkyl group is as previously described. The bond to the parent moiety is through the carbonyl.

"Alkylsulfonyl" means an alkyl-$SO_2$— group in which the alkyl group is as previously described. The bond to the parent moiety is through the sulfonyl.

"Arylsulfonyl" means an aryl-$SO_2$— group in which the aryl group is as previously described. The bond to the parent moiety is through the sulfonyl.

"Arylalkylsulfonyl" means an arylalkyl-$SO_2$— group in which the arylalkyl group is as previously described. The bond to the parent moiety is through the sulfonyl.

"Heteroarylsulfonyl" means a heteroaryl-$SO_2$— group in which the heteroaryl group is as previously described. The bond to the parent moiety is through the sulfonyl.

"Heteroarylalkylsulfonyl" means a heteroarylalkyl-$SO_2$— group in which the heteroarylalkyl group is as previously described. The bond to the parent moiety is through the sulfonyl.

"Alkoxycarbonyl" means an alkyl-O—C(O)— group in which the alkyl group is as previously described. The bond to the parent moiety is through the carbonyl.

"Aryloxycarbonyl" means an aryl-O—C(O)— group in which the aryl group is a previously described. The bond to the parent moiety is through the carbonyl.

"Arylalkoxycarbonyl" means an aralkyl-O—C(O)— group in which the arylalkyl group is a previously described. The bond to the parent moiety is through the carbonyl.

"Hydroxyalkyl" means a HO-alkyl-group in which alkyl is as previously defined. The bond to the parent moiety is through the alkyl group.

"Aminoalkyl" means a $NH_2$-alkyl group in which alkyl is as previously defined. The bond to the parent moiety is through the alkyl group. Substitution on the aminoalkyl may be at the alkyl hydrogens and/or at the amino hydrogens.

"Polyalkenyl" means an aliphatic hydrocarbon group containing at least two carbon-carbon double bonds and which may be straight or branched and comprises about 4 to about 12 carbon atoms in the chain, preferably about 4 to about 8 carbon atoms in the chain. Branched means that one or more lower alkyl groups such as methyl, ethyl or propyl or lower alkenyl groups, are attached to a linear alkenyl chain. The polyalkenyl can be optionally substituted by one or more substituents which may be the same or different, each substituent being independently selected from those described herein.

"Polyalkynyl" means an aliphatic hydrocarbon group containing at least two carbon-carbon triple bonds and which may be straight or branched and comprises about 4 to about 12 carbon atoms in the chain, preferably about 4 to about 8 carbon atoms in the chain. Branched means that one or more lower alkyl groups such as methyl, ethyl or propyl or lower alkynyl groups, are attached to a linear alkynyl chain. The polyalkynyl can be optionally substituted by one or more substituents which may be the same or different, each substituent being independently selected from those described herein.

"Substituent" means halogen, hydroxy, amino, thiol, alkyl, alkenyl, polyalkenyl, alkynyl, polyalkynyl, aryl, heteroaryl, haloalkyl, haloalkenyl, cycloalkyl, halocycloalkyl, heterocyclyl, hydroxyalkyl, alkoxy, aryloxy, arylalkoxy, cycloalkyloxy, haloalkoxy, alkoxycarbonyl, aryloxycarbonyl, arylalkoxycarbonyl, heteroaryloxycarbonyl, heteroarylalkoxycarbonyl, alkylsulfonyl, arylsulfonyl, arylalkylsulfonyl, heteroarylsulfonyl, heteroarylalkylsulfonyl, alkylthio, cycloalkylthio, arylthio, heteroarylthio, arylalkylthio, heteroarylalkylthio, —NHY$_1$, —NY$_1$Y$_2$ or —N$^+$Y$_1$Y$_2$Y$_3$, wherein Y$_1$, Y$_2$ and Y$_3$ are the same or different and each is an alkyl as described herein.

"Substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and uses as described herein.

"Optionally substituted" means optional substitution with the specified groups, radicals or moieties.

It is appreciated that the unsymmetrical cyanine dyes described herein may contain chiral centers. In those cases, all stereoisomers are understood to be included in the description of these cyanine dye structures, unless otherwise indicated. Such stereoisomers include pure optically active isomers, racemic mixtures, and mixtures of diastereomers containing any relative amount of one or more stereoisomeric configurations.

It is also appreciated that the unsymmetrical cyanine dyes described herein may contain geometric centers. In those cases, all geometric isomers are understood to be included in the description of the cyanine dye structures, unless otherwise indicated. Such geometric isomers include cis, trans, E and Z isomers, either in pure in various mixtures of geometric configurations. It is also understood that depending upon the nature of the double bond contained in the cyanine dye structures, such double bond isomers may interconvert between cis and trans, or between E and configurations depending upon the conditions, such as solvent composition, solvent polarity, ionic strength, and the like.

It is further appreciated that since the positive charge on the benzazolium portion of the unsymmetrical cyanine dyes described herein is 1 and the positive charge on the purinium or quinazolinium portion of the unsymmetrical cyanine dyes described herein is 1 to 3, several tautomers of the compounds of Formula I may exist, including mixtures of such tautomers. Illustratively, the charge may be formally localized on the nitrogen atom as depicted in Formula I, or on one of the carbon atoms forming the alkylene linker that connects the two heterocycles, or alternatively, the charge may be localized on the purinium or quinazolinium heterocycle. Tautomers of the charged compounds of Formula I may be depicted by rearranging the double bond-single bond configuration of compounds of Formula I. The unsymmetrical cyanine dyes described herein include any of the several possible tautomers, or various equilibrium mixtures of those tautomers. It is understood that the location of the formal charge is influenced by the nature of the moieties of the dyes. It is further understood that the favored tautomer or equilibrium mixture of tautomers may depend upon conditions, such as solvent composition, solvent polarity, ionic strength, formulation, and the like. It is understood that the term "resonance structures" also refers to these various charge localizations and is equally descriptive of formulae illustrated above.

It is also understood that since the compounds of Formula I carry a net charge, these compounds of Formula I are accompanied by a counter ion. Any monovalent, divalent, or polyvalent counter ion is included in the description of the cyanine dye structures contained herein. Illustrative counter-ions include negatively charged counter ions such as iodide, chloride, bromide, hydroxide, oxide, acetate, trifluoroacetate, monophosphate, diphosphate, triphosphate, and the like. Such counter ions may arise from the synthetic methods used, the purification protocol, or other ion exchange processes.

It is believed that the nature or type of counter ion does not appear to influence the functionality of the cyanine dyes described herein. It is appreciated that when the dyes described herein are dissolved in solvents or other media used to practice the amplification reactions, such as PCR, the accompanying counter ion may exchange with other counter ions that are present in the solvents or other media. Such additional counter ions may be solvent ions, salts, buffers, and/or metals.

It should also be noted that any carbon as well as heteroatom with unsatisfied valences in the text, schemes, examples and Tables herein is assumed to have the sufficient number of hydrogen atom(s) to satisfy the valences. In addition, it should also be noted that tautomeric forms are considered equivalent in certain embodiments of this invention.

In one embodiment, the positive charge(s) on $R_1$ and/or $R_2$, or on $R_3$, and/or $R_4$, and/or $R_5$, and/or $R_6$ and/or $R_7$ arises from a substituent on the unsymmetrical cyanine dye that has a positive charge in the native configuration. In another embodiment, the positive charge(s) on $R_1$ and/or $R_2$, or on $R_3$, and/or $R_4$, and/or $R_5$, and/or $R_6$ and/or $R_7$ arises from a substituent substituents that have a positive charge at the pH for which an amplification reaction, such as a polymerase chain reaction, is conducted.

In one embodiment, A has the structure of Formula II. In some embodiments, $R_1$ is aryl, alkyl substituted with dialkylamino, alkyl substituted with trialkylamino, alkyl substituted with alkoxy, alkyl substituted with alkoxy that is substituted with dialkylamino, or alkyl substituted with an N-substituted heterocyclyl, and $R_2$ is hydrogen, alkyl, thiol, alkyl substituted with trialkylamino or alkyl substituted with alkoxy.

In another embodiment, A has the structure of Formula III. In some embodiments, $R_3$ is hydrogen, methyl, alkyl substituted with trialkylamino or alkyl substituted with an N-substituted heterocyclyl, $R_4$ is hydrogen, alkyl, aryl, thiol, alkyl substituted with dialkyamino, alkyl substituted with trialkylamino, alkyl substituted with alkoxy that is substituted with dialkylamino, or alkyl substituted with an N-substituted heterocyclyl, $R_5$ is hydrogen, halo, alkyl, aryl or alkyl substituted with alkoxy that is substituted with dialkylamino, $R_6$ is hydrogen, alkyl, alkyl substituted with trialkylamino or alkyl substituted with an N-substituted heterocyclyl and $R_7$ is hydrogen, alkyl or alkyl substituted with alkoxy.

Unsymmetrical cyanine dyes of the present invention can be prepared by a general method that attaches the benzazolium portion of the molecule to the purinium or quinazolinium portion through a methine group (—C(H)═). In the synthesis of the unsymmetrical cyanine dyes described herein, a combination of precursors is used to produce the compounds of Formula I. For example, the benzazolium precursor is a compound of Formula IV

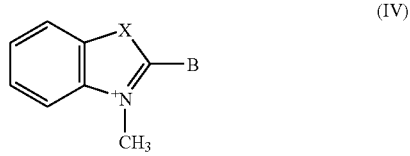

(IV)

which is reacted with a purinium compound of Formula V

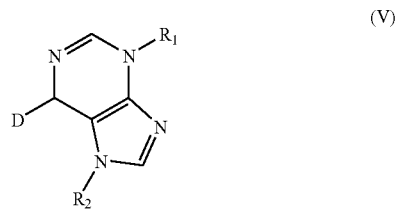

(V)

or a quinazolinium compound of Formula VI

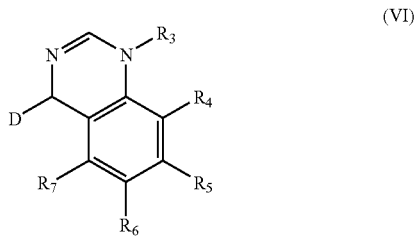

(VI)

in which either B or D is methyl and the other of B or D is a reactive leaving group that is typically methylthio, methylsulfonyl, or chloro, but which can be any leaving group that provides sufficient reactivity to complete the reaction.

The chemistry required to prepare and combine these precursors is well understood by one skilled in the art (e.g., U.S. Pat. No. 4,937,198; Neiman et al., *Israel J Chem* 3:161 (1965); Brooker et al., *J Am Chem Soc* 67:1889 (1945); Brooker et al., *J Am Chem Soc* 64:199 (1942)). For example, the benzazolium portion can be prepared by techniques known in the art (e.g., Brooker et al., *J Am Chem Soc* 64:199 (1942)) or can be obtained commercially. The purinium or quinazolinium portions can be prepared by techniques well known in the art. Typically, 6(methyl) purine or 6(methylthio) purine for the purinium portion or optionally substituted 4(methyl)quinazoline or optionally 4(methylthio)quinazoline for the quinazolinium portion is alkylated prior to combination with the benzazolium portion by conventional techniques, such as alkylating the parent heterocycle with appropriate alkylating agents, such as $R_1$—Z, $R_2$—Z or $R_3$—Z, wherein $R_1$, $R_2$ and $R_3$ are as previously described and Z is an electronegative group. The electronegative group is typically iodide, methane sulfonate, methyl sulfate, trifluoromethanesulfonate or p-toluenesulfonate, but which can be any electronegative group that provides sufficient reactivity to complete the reaction.

In a second aspect, the present invention provides a method of performing nucleic acid analysis in the presence of the novel unsymmetrical cyanine dyes of the present invention. In one embodiment, the method comprises the steps of: mixing an unsymmetrical cyanine dye of the present invention with a sample comprising a target nucleic acid and one or more primers configured for amplifying the target nucleic acid, amplifying the target nucleic acid in the presence of the unsymmetrical cyanine dye, and monitoring fluorescence of the unsymmetrical cyanine dye. In another embodiment, the monitoring step comprises melting the amplified target nucleic acid to generate a melting curve. In a further embodiment, the target nucleic acid comprises a single nucleotide polymorphism. In an additional embodiment, the method further comprises identifying a genotype on the basis of the monitored fluorescence. In one embodiment, the genotype is identified on the basis of the melting curve. In another embodiment, the amplification and monitoring occur in a microfluidic channel. In one embodiment, the monitoring step occurs during the amplification step. In another embodiment, the monitoring step occurs subsequent to the amplification step. In a further embodiment, the monitoring occurs during the amplification step and subsequent to the amplification step. In one embodiment, the monitoring step subsequent to the amplification step comprises melting the amplified target nucleic acid to generate a melting curve.

These various embodiments of nucleic acid analysis are performed using techniques well known in the art by substituting the novel unsymmetrical cyanine dyes of the present invention for the dyes used in such known techniques. For example, melting curve analysis using the dyes of the present invention can be performed in instruments or in microchannels such as described by Knight et al. (U.S. Patent Application Publication No. 2007/0231799), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Wittwer et al. (U.S. Patent Application Publication No. 2007/0020672) and Sundberg et al. (U.S. Patent Application Publication No. 2007/0026421). Amplification of nucleic acids using the dyes of the present invention can be performed in instruments or in microchannels such as described by Knight et al. (U.S. Patent Application Publication No. 2007/0231799), Hasson et al. (U.S. Patent Application Publication No. 2008/0003588), Hasson et al. (U.S. Patent Application Publication No. 2008/0130971), Owen et al. (U.S. Patent Application Publication No. 2008/0176230), Wittwer et al. (U.S. Patent Application Publication No. 2007/0020672), and Sundberg et al. (U.S. Patent Application Publication No. 2007/0026421). Amplifications of nucleic acids and melting analysis with monitoring during each phase can be performed in instruments or in microchannels such as described by Knight et al. (U.S. Patent Application Publication No. 2007/0231799), Hasson et al. (U.S. Patent Application Publication No. 2008/0130971) and Owen et al. (U.S. Patent Application Publication No. 2008/0176230). The dyes of the present invention can be used in combination with other known dyes for multiplexing reactions such as described in the previously identified published U.S. patent applications. These techniques are useful for determining identifying the presence or absence of a particular nucleic acid, identifying the presence of single nucleotide polymorphisms, identifying a genotype, distinguishing homozygotes and heterozygotes, genotyping nucleic acids, mutation scanning and the like.

EXAMPLES

The present invention is described by reference to the following Examples, which are offered by way of illustration and are not intended to limit the invention in any manner. Standard techniques well known in the art or the techniques specifically described below were utilized.

Example 1

Synthesis of a New Purinium Based Dye S1 (4)

1. Synthesis of 2-[2-(dimethylamino)ethoxy]p-toluenesulfonate (1)

A round bottomed flask is charged with 1.33 g of 2-[2-(dimethylamino)ethoxy]ethanol (Sigma) and 1.9 g of p-toluenesulfonyl chloride in 50 ml $CH_2Cl_2$ solvent. The mixture is heated in an oil bath at 40° C. for 1 hour. A white crystalline solid precipitates from the solution. The crystalline solid is 2-[2-(dimethylamino)ethoxy]p-toluenesulfonate (1).

2. Synthesis of 3-{2-[2-(dimethylamino)ethoxy]}-6-(methylthio)purine (2)

5.74 g of the 2-[2-(dimethylamino)ethoxy]p-toluenesulfonate (1), 3.7 g of 6(methylthio)purine (from sigma) and 20 ml of dimethylformide are mixed in a round bottomed flask and heated in an oil bath at 110° C. for 3 hours. After cooling, 10 ml of water is added to the solution which then is extracted with three 20 ml portions of benzyl acetate to remove unreacted starting reagent. The pH of the aqueous solution is adjusted to 11 with the addition of NaOH. A white solid crystalline material which is unreacted starting material precipitates from solution. After removing this crystalline unreacted starting material, the pH of the solution is adjusted to 14. A white crystalline solid precipitates from solution which is 2-[2-(dimethylamino)ethoxy]-6-(methylthio)purine (2).

3. Synthesis of 3-{2-[2-(dimethylamino)ethoxy]}7-methyl-6-(methylthio)purine (3)

In a round bottomed flask, 3.1 g of 3-{2-[2-(dimethylamino)ethoxy]}-6-(methylthio)purine (2) is mixed with 1.9 g of methyl p-toluensulfonate in solvent. The mixture is heated in an oil bath at 100° C. for 2 hours. The solution is cooled down and washed with acetone and ether. A white amorphous solid material precipitates from the organic washes. The solid is 3-{2-[2-(dimethylamino)ethoxy]}7-methyl-6-(methylthio)purine (3).

4. Synthesis of New Purinium Based Dye S1 of Structure (4)

In a round bottom flask, 3.0 g of -{2-[2-(dimethylamino) ethoxy]}7-methyl-6-(methylthio)purine(3) is mixed with 1.4 g of 2,3-dimethylbenzothiazolium iodide(Sigma), 20 ml of methanol and 0.5 ml of triethylamine. The mixture is refluxed for 1 hour. After cooling, the mixture is filtered and washed with methanol and benzyl acetate to produce the named compound as a yellow-orange solid. The synthesis of the new dye is shown in Scheme 1.

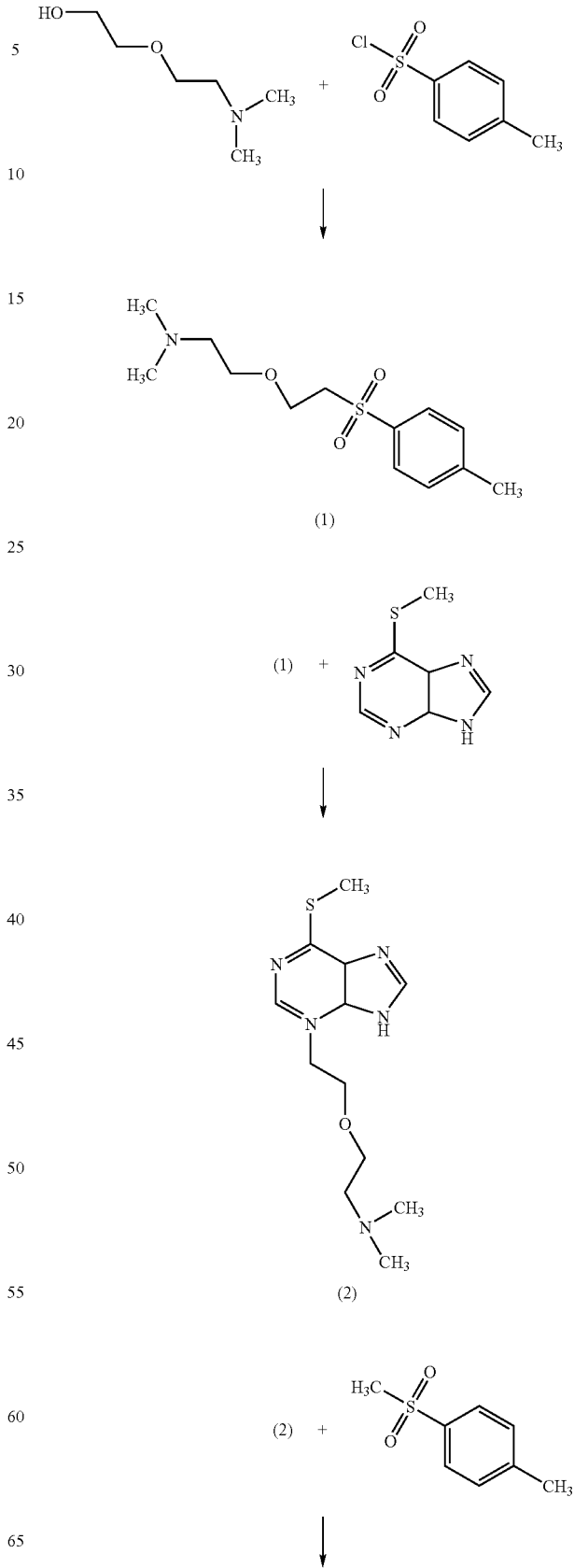

Scheme 1

-continued

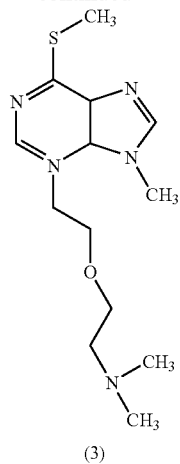

(3)

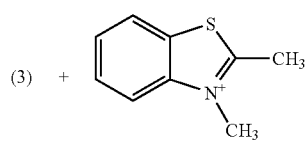

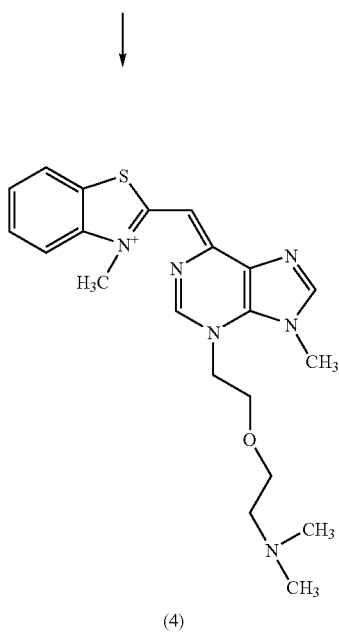

(4)

Examples 2-13

Synthesis of New Purinium Based Dyes

Purinium based dyes having the following formula with substituents as shown in Table 1 are synthesized analogously to the new dye in Example 1 using the appropriate starting materials. $R_1$ and/or $R_2$ will have a positive charge at the pH of the polymerase chain reaction, which is typically between approximately 7 and 8.

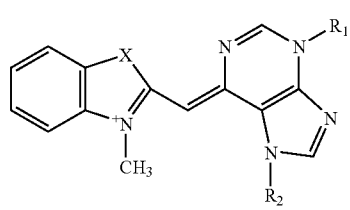

TABLE 1

| Dyes | X | $R_1$ | $R_2$ |
|---|---|---|---|
| S2 | S | $H_2C-CH_2-N(CH_3)-CH_3$ | Me |
| S3 | S | Phenyl | $H_2C-N^+(CH_3)_3$ |
| S4 | S | $H_2C-CH_2-N(CH_3)-CH_3$ | Me |
| S5 | S | $H_2C-CH_2-\text{(4-methylpiperidinyl)}$ | Me |
| S6 | S | $H_2C-N^+(CH_3)_3$ | $H_2C-O-CH_2CH_3$ |
| S7 | S | $H_2C-CH_2-\text{(4-methylpiperidinyl)}$ | SH |
| S8 | S | $H_2C-O-CH_2CH_2-N(CH_3)_2$ | $H_2C-N^+(CH_3)_3$ |
| O1 | O | $H_2C-CH_2-N(CH_3)-CH_3$ | H |
| O2 | O | $H_2C-CH_2-N(CH_3)-CH_3$ | Me |
| O3 | O | $H_2C-N^+(CH_3)_3$ | Me |
| O4 | O | $H_2C-CH_2-N(CH_3)-CH_3$ | $H_2C-N^+(CH_3)_3$ |
| O5 | O | $H_2C-CH_2-\text{(4-methylpiperidinyl)}$ | Me |

Example 14

Synthesis of a New Quinazolinium Based Dye S9 (5)

The new quinazolinium dye S9 is prepared as in steps (1), (2) and (4) of Example 1 except that 4(methylthio)quinazoline is used in place of 6(methylthio)purine in step 2 to yield the dye of structure 5.

Examples 15-26

Synthesis of New Quinazolinium Based Dyes

Dyes having the following formula with substituents as shown in Tables 2-4 are synthesized analogously to the dye in Example 14 using the appropriate starting materials. $R_3$ and/or $R_4$ and/or $R_5$ and/or $R_6$ and/or $R_7$ will have a positive charge at the pH of the polymerase chain reaction, which is typically between approximately 7 and 8.

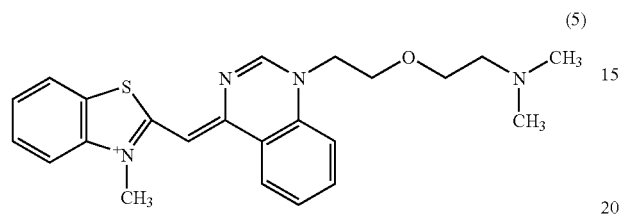

(5)

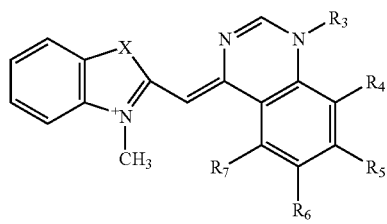

TABLE 2

| Dye | X | $R_3$ | $R_4$ | $R_5$ | $R_6$ | $R_7$ |
|---|---|---|---|---|---|---|
| S10 | S | Me | | H₂C–CH₂–N(CH₃)–CH₃ | H | Me | H |
| S11 | S | H₃C–N⁺(CH₃)(CH₃)–CH₂– | Phenyl | Me | H | Me |
| S12 | S | Me | H | H₂C–CH₂–O–CH₂–CH₂–N(CH₃)–CH₃ | H | H |
| S15 | S | H₂C–(4-piperidyl N–CH₃) | SH | Me | Me | Me |
| S16 | S | H₃C–N⁺(CH₃)(CH₃)–CH₂– | H₂C–CH₂–O–CH₂–CH₂–N(CH₃)–CH₃ | Phenyl | H | H |
| O6 | O | H | | H₂C–CH₂–N(CH₃)–CH₃ | H | H | H |
| O8 | O | Me | | H₃C–N⁺(CH₃)(CH₃)–CH₂– | H | H | H |
| O9 | O | H₃C–N⁺(CH₃)(CH₃)–CH₂– | H₂C–CH₂–N(CH₃)–CH₃ | H | Me | H |
| O10 | O | Me | H₂C–(4-piperidyl N–CH₃) | | H | H | Me |

TABLE 3

| Dye | X | R₃ | R₄ | R₅ | R₆ | R₇ |
|-----|---|----|----|----|----|----|
| S13 | S | Me | Me | H | H₂C-CH₂-(piperidine)-N-CH₃ | H |
| S14 | S | H₃C-N⁺(CH₃)(CH₃)-CH₂- | H | Cl | H | H₂C-O-CH₃ |

TABLE 4

| Dye | X | R₃ | R₄ | R₅ | R₆ | R₇ |
|-----|---|----|----|----|----|----|
| O7 | O | Me | H₂C-CH₂-N(CH₃)-CH₃ | H | H₃C-N⁺(CH₃)(CH₃)-CH₂- | H |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. An unsymmetrical cyanine dye having the Formula I

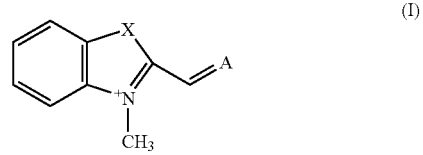

wherein A is

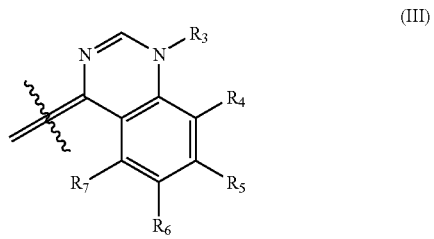

wherein
X is O or S;
$R_3$, $R_4$, $R_5$, $R_6$ and $R_7$ are independently hydrogen, halogen, thiol, optionally substituted alkyl, optionally substituted alkoxy, optionally substituted alkenyl, optionally substituted polyalkenyl, optionally substituted alkynyl, optionally substituted polyalkynyl, optionally substituted thioalkyl, optionally substituted aminoalkyl, optionally substituted aryl, optionally substituted heteroaryl and optionally substituted arylalkyl;
and further wherein $R_3$, and/or $R_4$, and/or $R_5$, and/or $R_6$ and/or $R_7$ carry one or more positive charges such that the sum of the positive charge(s) on $R_3$, $R_4$, $R_5$, $R_6$ and $R_7$ is 1, 2 or 3.

2. The unsymmetrical cyanine dye of claim 1, wherein $R_3$ is hydrogen, methyl, alkyl substituted with trialkylamino or alkyl substituted with an N-substituted heterocyclyl.

3. The unsymmetrical cyanine dye of claim 1, wherein $R_4$ is hydrogen, alkyl, aryl, thiol, alkyl substituted with dialkyamino, alkyl substituted with trialkylamino, alkyl substituted with alkoxy that is substituted with dialkylamino, or alkyl substituted with an N-substituted heterocyclyl.

4. The unsymmetrical cyanine dye of claim 1, wherein $R_5$ is hydrogen, halo, alkyl, aryl or alkyl substituted with alkoxy that is substituted with dialkylamino.

5. The unsymmetrical cyanine dye of claim 1, wherein $R_6$ is hydrogen, alkyl, alkyl substituted with trialkylamino or alkyl substituted with an N-substituted heterocyclyl.

6. The unsymmetrical cyanine dye of claim 1, wherein $R_7$ is hydrogen, alkyl or alkyl substituted with alkoxy.

7. The unsymmetrical cyanine dye of claim 1, wherein
$R_3$ is hydrogen, methyl, alkyl substituted with trialkylamino or alkyl substituted with an N-substituted heterocyclyl,
$R_4$ is hydrogen, alkyl, aryl, thiol, alkyl substituted with dialkyamino, alkyl substituted with trialkylamino, alkyl substituted with alkoxy that is substituted with dialkylamino, or alkyl substituted with an N-substituted heterocyclyl,
$R_5$ is hydrogen, halo, alkyl, aryl or alkyl substituted with alkoxy that is substituted with dialkylamino,
$R_6$ is hydrogen, alkyl, alkyl substituted with trialkylamino or alkyl substituted with an N-substituted heterocyclyl and
$R_7$ is hydrogen, alkyl or alkyl substituted with alkoxy.

8. The unsymmetrical cyanine dye of claim 1, wherein the 1, 2 or 3 positive charges on $R_3$, $R_4$, $R_5$, $R_6$ and $R_7$ are present in the native dye.

9. The unsymmetrical cyanine dye of claim 1, wherein the 1, 2 or 3 positive charges on $R_3$, $R_4$, $R_5$, $R_6$ and $R_7$ are present in the dye at a pH of an amplification reaction.

10. A method of nucleic acid analysis comprising the steps of: mixing an unsymmetrical cyanine dye of claim 1 with a sample comprising a target nucleic acid and one or more primers configured for amplifying the target nucleic acid, amplifying the target nucleic acid in the presence of the unsymmetrical cyanine dye, and monitoring fluorescence of the unsymmetrical cyanine dye.

11. The method of claim 10, wherein the monitoring step comprises melting the amplified target nucleic acid to generate a melting curve.

12. The method of claim 10, wherein the target nucleic acid comprises a single nucleotide polymorphism.

13. The method of claim 10 which further comprises identifying a genotype on the basis of the monitored fluorescence.

14. The method of claim 11 which further comprises identifying a genotype on the basis of the melting curve.

15. The method of claim 10, wherein the amplification and monitoring occur in a microfluidic channel.

16. The method of claim 10, wherein the monitoring step occurs during the amplification step.

17. The method of claim 10, wherein the monitoring step occurs subsequent to the amplification step.

18. The method of claim 10, wherein the monitoring occurs during the amplification step and subsequent to the amplification step.

19. The method of claim 18, wherein the monitoring step subsequent to the amplification step comprises melting the amplified target nucleic acid to generate a melting curve.

* * * * *